(12) United States Patent
da Silva Curiel et al.

(10) Patent No.: US 9,744,076 B2
(45) Date of Patent: Aug. 29, 2017

(54) METHOD AND APPARATUS FOR INSERTING AN IMPLANT IN THE CORNEA OF THE EYE

(71) Applicants: Jeannette M. A. da Silva Curiel, Camarillo, CA (US); William R. Taber, Camarillo, CA (US)

(72) Inventors: Jeannette M. A. da Silva Curiel, Camarillo, CA (US); William R. Taber, Camarillo, CA (US)

( * ) Notice: Subject to any disclaimer, the term of this patent is extended or adjusted under 35 U.S.C. 154(b) by 0 days.

(21) Appl. No.: 15/072,336

(22) Filed: Mar. 16, 2016

(65) Prior Publication Data
US 2016/0270958 A1 Sep. 22, 2016

Related U.S. Application Data

(60) Provisional application No. 62/133,955, filed on Mar. 16, 2015.

(51) Int. Cl.
*A61M 5/00* (2006.01)
*A61F 9/007* (2006.01)

(52) U.S. Cl.
CPC .. *A61F 9/00781* (2013.01); *A61F 2220/0008* (2013.01)

(58) Field of Classification Search
CPC .................. A61F 9/00781; A61F 2202/0008
USPC ....................................................... 604/8–9
See application file for complete search history.

(56) References Cited

U.S. PATENT DOCUMENTS

| | | | |
|---|---|---|---|
| 3,788,327 A | 1/1974 | Donowitz | |
| 4,729,761 A | 3/1988 | White | |
| 5,092,837 A * | 3/1992 | Ritch | A61F 9/00781 604/294 |
| 5,300,020 A | 4/1994 | L'Esperance, Jr. | |
| 5,411,473 A | 5/1995 | Ahmed | |
| 5,626,558 A | 5/1997 | Suson | |
| 5,626,559 A | 5/1997 | Solomon | |
| 5,702,414 A * | 12/1997 | Richter | A61F 9/00781 606/108 |
| 5,743,868 A | 4/1998 | Brown et al. | |
| 5,807,302 A * | 9/1998 | Wandel | A61F 9/00781 604/8 |
| 6,007,511 A | 12/1999 | Prywes | |

(Continued)

OTHER PUBLICATIONS

International Search Report for PCT/US16/22721 mailed Aug. 12, 2016.

*Primary Examiner* — Philip R Wiest
(74) *Attorney, Agent, or Firm* — Brooks Acordia IP Law, P.C.; Pejman Yedidsion

(57) ABSTRACT

Methods, devices, and systems for inserting an implant in the cornea (105) of the eye, where the implant is a microshunt device (405,515). The microshunt device may comprise an inlet (425) section comprising at least one lumen and at least one inlet opening; an outlet (420) section comprising at least one lumen that connects to at least one outlet opening; and where the microshunt device (405,515) is configured to be implanted within the cornea (105) of an eye, where the microshunt device effects the flow of aqueous humor from an anterior chamber (160,235) of the eye to the anterior surface of the cornea (410,630), bypassing the trabecular meshwork (145,240), thereby diverting aqueous humor from the anterior chamber (160,235) to the surface of the cornea (410,630).

3 Claims, 7 Drawing Sheets

(56) References Cited

U.S. PATENT DOCUMENTS

| | | | |
|---|---|---|---|
| 6,203,513 B1 * | 3/2001 | Yaron | A61F 9/00781 604/264 |
| 6,533,768 B1 * | 3/2003 | Hill | A61F 9/00781 604/521 |
| 7,879,001 B2 | 2/2011 | Haffner et al. | |
| 7,947,008 B2 | 5/2011 | Grahn et al. | |
| 8,333,742 B2 | 12/2012 | Bergheim et al. | |
| 8,444,588 B2 | 5/2013 | Yablonski | |
| 8,603,024 B2 | 12/2013 | Bohm et al. | |
| 8,734,378 B2 | 5/2014 | De Juan, Jr. et al. | |
| 8,808,219 B2 | 8/2014 | Bergheim et al. | |
| 8,852,256 B2 | 10/2014 | Horvath et al. | |
| 2006/0173397 A1 | 8/2006 | Tu et al. | |
| 2007/0149915 A1 | 6/2007 | Yablonski | |
| 2007/0156079 A1 | 7/2007 | Brown | |
| 2007/0276316 A1 | 11/2007 | Haffner et al. | |
| 2008/0161741 A1 | 7/2008 | Bene et al. | |
| 2009/0043242 A1 | 2/2009 | Bene et al. | |
| 2009/0177138 A1 | 7/2009 | Brown et al. | |
| 2012/0123317 A1 | 5/2012 | Horvath et al. | |
| 2013/0267887 A1 | 10/2013 | Kahook et al. | |
| 2014/0012177 A1 | 1/2014 | Tu et al. | |
| 2014/0243729 A1 | 8/2014 | Rynerson | |
| 2014/0276332 A1 | 9/2014 | Crimaldi et al. | |
| 2015/0011926 A1 | 1/2015 | Reitsamer et al. | |

\* cited by examiner

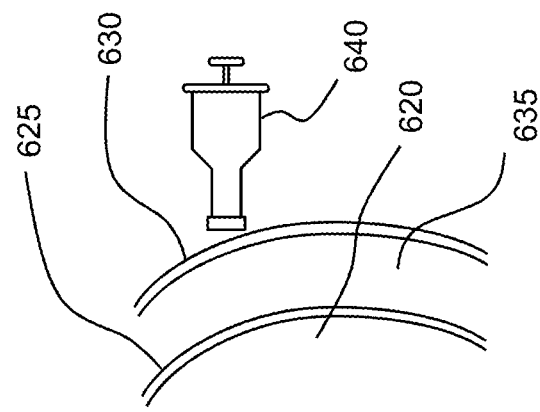
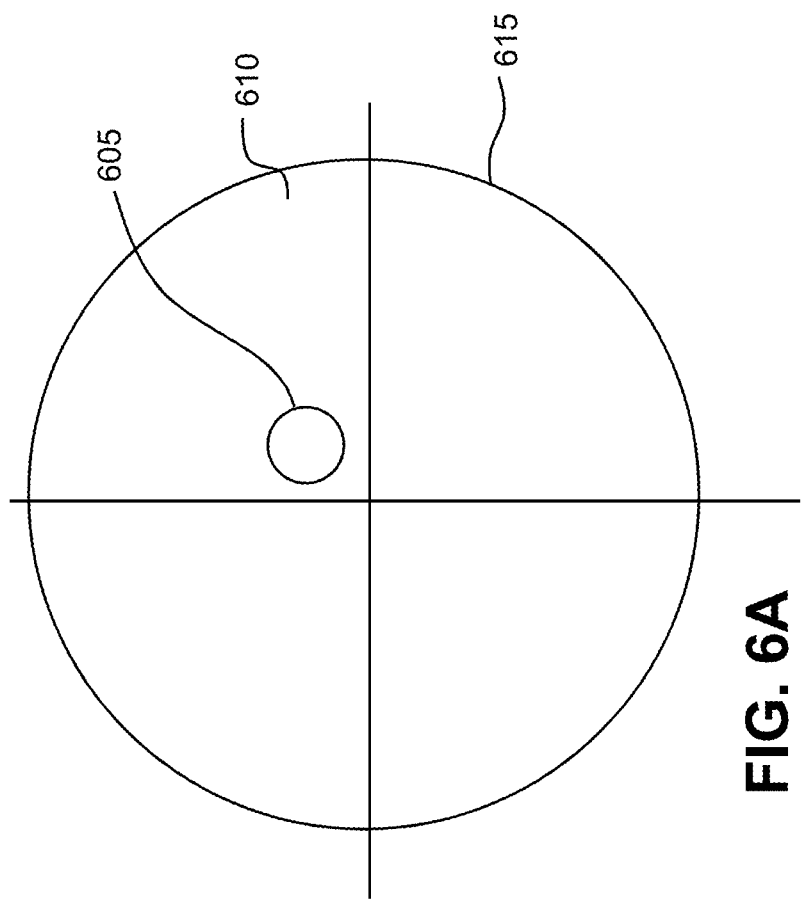
FIG. 6B
FIG. 6A

METHOD AND APPARATUS FOR INSERTING AN IMPLANT IN THE CORNEA OF THE EYE

CROSS-REFERENCE TO RELATED APPLICATIONS

This application claims priority to and benefit of Provisional Patent Application No. 62/133,955 filed Mar. 16, 2015 and is hereby incorporated by reference for all purposes.

TECHNICAL FIELD

The invention, in its several embodiments, pertains to medical devices for control of glaucoma and/or dry eye, and more particularly to a method and apparatus for inserting a glaucoma implant in the cornea of the eye.

BACKGROUND

Glaucoma is a term describing a group of eye disorders caused when the intraocular pressure within the eye increases, thereby causing retinal and optic nerve damage and subsequent loss of vision. The anterior chamber is the cavity located between the cornea and the lens, and is filled with a fluid (i.e., aqueous). Aqueous fluid is continuously produced by secretions from the ciliary body. The aqueous drains from the anterior chamber through the drainage angle and into the venous system. In a normal situation, aqueous production is equal to aqueous outflow through the drainage angle (angle), and intraocular pressure remains fairly constant in a range considered to be safe, for example, 15 to 21 mmHg range. Glaucoma occurs when aqueous does not drain sufficiently from the anterior chamber through the angle, causing an increase in intraocular pressure above the safe range. Raised intraocular pressure (generally above 21 mm Hg in humans and above 28 mm Hg in cats, dogs, and horses) is the most important and currently the only modifiable risk factor for treating glaucoma. Lowering this intraocular pressure is the major treatment goal in all glaucoma patients.

In the human eye, aqueous drains from the anterior chamber through the trabecular meshwork into a collecting channel, called Schlemm's canal. From Schlemm's canal, aqueous flows into collector channels that join Schlemm's canal, and then into the episcleral venous system. However, the anatomy of the canine, feline, and equine iridocorneal drainage angle has significant differences compared with the human eye. These eyes have pillars of tissue (pectinate ligaments) as the most anterior part of the iridocorneal angle, which communicate with a wide region (the ciliary cleft) that drains aqueous into the uveal and corneoscleral trabecular meshwork. From there, aqueous enters into one or more drainage veins that comprise the angular aqueous plexus (AAP), and then exits the eye via episcleral veins.

In all species, glaucoma can be roughly divided into two main categories, "open-angle" (or OAG) and "closed angle" or "angle-closure" (or ACG) glaucoma. In open-angle glaucoma, the anterior chamber remains open, but the exit of aqueous through the trabecular meshwork is reduced. Closed-angle glaucoma is caused by closure of the angle, preventing drainage of aqueous out of the anterior chamber.

Glaucoma can also be classified as "primary" (inherited) and "secondary" (non-inherited). Secondary glaucoma can be caused by injury, abnormal structures, inflammation, tumors, certain drugs, or diseases. Both primary and secondary glaucoma can be open or closed angle.

Despite its importance, the long-term control of human and veterinary glaucoma continues to be a challenge and is often unsuccessful in controlling the glaucoma and/or maintaining vision. Current treatments for glaucoma include medications and/or surgery to decrease intraocular fluid production, increase fluid drainage from the eye, or both.

In both human and veterinary medicine, few advancements have been made in medical and surgical therapy for glaucoma. Medical and surgical treatment is expensive and unaffordable to a large majority of human and veterinary glaucoma patients. Medications can cause side effects and are frequently ineffective in long-term control of glaucoma. When drug therapy fails, surgical therapy is needed.

Various forms of surgery to treat glaucoma include methods to open the fluid drainage channels, reduce fluid production by the ciliary body, or both. Multiple surgeries may be required, and frequently medications are also needed to help control intraocular pressure postoperatively.

In humans, there are many different surgical procedures for control of open-angle glaucoma. These surgeries involve procedures that mechanically disrupt the trabecular meshwork, improve outflow of aqueous through the drainage angle, making holes in the peripheral iris, filtering procedures (penetrating or non-penetrating), tube shunts (valved or non-valved), reduce aqueous fluid production, or involve manipulations of Schlemm's canal These surgeries are all major operations that are designed for treatment of open-angle glaucoma, Most of these surgical techniques are not applicable for the canine, feline, or equine eye because of the lack of Schlemm's canal in these species, because they are designed mainly for the treatment of open-angle glaucoma rather than closed-angle glaucoma.

Various tube-shunt drainage devices have been developed for treatment of closed-angle glaucoma and divert aqueous fluid out of the eye to the subconjunctival space (Ahmed valve, Molteno glaucoma shunt) or into the frontal sinus or nasal cavity (Cullen shunt) Shunt surgeries eventually fail due to clogging of the drainage tube, and/or due to formation of a fibrous tissue capsule over the shunt, causing decreased flow of aqueous fluid out of the eye. This causes return of glaucoma and necessitates further treatment.

All of the above surgeries have numerous disadvantages including poor long-term prognosis for control of glaucoma. They need to be performed in an operating room, involve substantial trauma to the eye, require great surgical skill, have the potential for significant complications, are expensive, and have limited to no availability for many pet owners. Most significantly, the anatomy of the canine, feline, and equine iridocorneal filtration angle has significant differences compared with the human eye, which renders most human glaucoma-management surgeries ineffective in dogs, cats, and/or horses Acute angle-closure glaucoma in dogs is an emergency and requires that the intraocular pressure be reduced to a safe range within minutes or hours. Glaucoma surgeries which attempt to preserve vision are often declined by clients because they may need to travel long distances to find a veterinary ophthalmologist that can provide such surgeries, the cost of surgery is very expensive, pre- and post-surgical treatments are time-consuming and expensive, and the patient may be uncooperative. If treatment is delayed, permanent blindness will usually occur, often within a matter of a few hours. In most dogs, glaucoma is also a very painful condition. Once the eye is blinded by glaucoma, then glaucoma-eliminating surgery (such as enucleation, i.e., removal, of the eye, evisceration of the eye with surgical placement of an intraocular prosthesis, or an ablation procedure) is required to restore comfort and eliminate the requirement for treatment. Therefore, new surgical approaches need to be developed that provide faster, better, safer, and less expensive care for both human and veterinary glaucoma patients, both in the short- and long-term.

SUMMARY

A device embodiment of the microshunt device may comprise: an inlet section comprising at least one lumen and at least one inlet opening; an outlet section comprising at least one lumen that connects to at least one outlet opening; and wherein the microshunt device is configured to be implanted within a cornea of an eye, wherein the microshunt device effects the flow of aqueous humor from an anterior chamber of the eye to the anterior surface of the cornea, bypassing the trabecular meshwork, thereby diverting aqueous humor from the anterior chamber to the surface of the cornea; and wherein the microshunt is prevented from migrating from an implantation site. The microshunt device may further comprise a plurality of lumens arranged in a series and parallel to each other. Optionally, the microshunt device may be retained, before implantation, via a plunger-type deployment mechanism. Additionally, the microshunt device may be deployed from an applicator and once a distal section of the applicator passes beyond a corneal endothelium and into the anterior chamber.

In another embodiment, the microshunt deployment may be facilitated by the plunger-type deployment mechanism with an associated deployment actuator mounted on a handle of the applicator. Optionally, the microshunt device may utilizes fluid flow from a higher pressure environment to a lower pressure environment. In one embodiment, the microshunt device may further comprise a flow-restricting member within the lumen that may be configured to: control globe decompression after the microshunt is implanted; and control flow of the aqueous humor out of the eye. Additionally, the flow-restricting member within the lumen may act to partially fill the lumen; and the flow-restricting member within the lumen may be a wire having a diameter thickness smaller than the lumen. In some embodiments, the flow-restricting member may be further configured to control the flow of aqueous humor based on thickness of diameter.

A system embodiment may comprise: a barrel holder, wherein the holder may have a proximal end and a distal end, wherein the proximal end of the holder contains a plunger and the distal end contains an extrusion tip; wherein the extrusion tip further comprises a first lumen and at least one irrigating hole disposed between the proximal and distal ends of the extrusion tip; wherein the irrigating hole is in fluid communication with the lumen; a microshunt device, wherein the microshunt device is configured to be implanted within a cornea of an eye, and wherein the microshunt effects the flow of aqueous humor from an anterior chamber of the eye to the anterior surface of the cornea, bypassing the trabecular meshwork; and a barrel holder comprising a second lumen, wherein a distal end of the second lumen opens to the distal end of the extrusion tip portion; and wherein the holder is configured to hold the microshunt device during implantation of the microshunt device within the eye, and the holder releases the microshunt device upon deployment of the microshunt device. Optionally, the proximal end of the second lumen may be separated from the first lumen of the extrusion tip. Additionally, fluid may be infused through a lumen of the microshunt into the anterior chamber. In one system embodiment, the system may further comprise a flow-restricting member configured to: control globe decompression after the microshunt is implanted; and control flow of aqueous out of the eye.

A method embodiment may comprise the steps of: providing a microshunt for diverting aqueous humor from the anterior chamber of a cornea to the surface of the cornea; providing an applicator for delivering the microshunt into the cornea; creating an incision in and through the cornea for the microshunt placement via a distal portion of the applicator comprising a cutting tool; placing tightly, the microshunt within the cannula lumen of the applicator, wherein the microshunt is retained by a plunger-type deployment mechanism; deploying the microshunt, from the applicator, once the distal section passes beyond the corneal endothelium and into the anterior chamber; and regulating the flow of the aqueous humor via the deployed microshunt once implanted, thereby the aqueous humor flows controllably from an anterior chamber of the eye to the anterior surface of the cornea, bypassing the trabecular meshwork. Optionally, securing the microshunt may be via a fastening mechanism.

The regulating of the flow of the aqueous humor via the deployed microshunt may further comprise employing a flow-restricting member. In one embodiment, the regulating of the flow of the aqueous humor via the deployed microshunt may further comprise: controlling globe decompression after the microshunt is deployed and implanted via the flow-restricting member. Additionally, the flow-restricting member may be a wire having a diameter thickness that is less than diameter thickness of the microshunt.

BRIEF DESCRIPTION OF DRAWINGS

The components in the figures are not necessarily to scale, emphasis instead being placed upon illustrating the principals of the invention. Like reference numerals designate corresponding parts throughout the different views. Embodiments are illustrated by way of example and not limitation in the figures of the accompanying drawings, in which:

FIG. 6A depicts a front view of a method by which the microshunt is implanted within the cornea;

FIG. 6B depicts a side view of a method by which the microshunt is implanted within the cornea.

DETAILED DESCRIPTION

Figure 1:
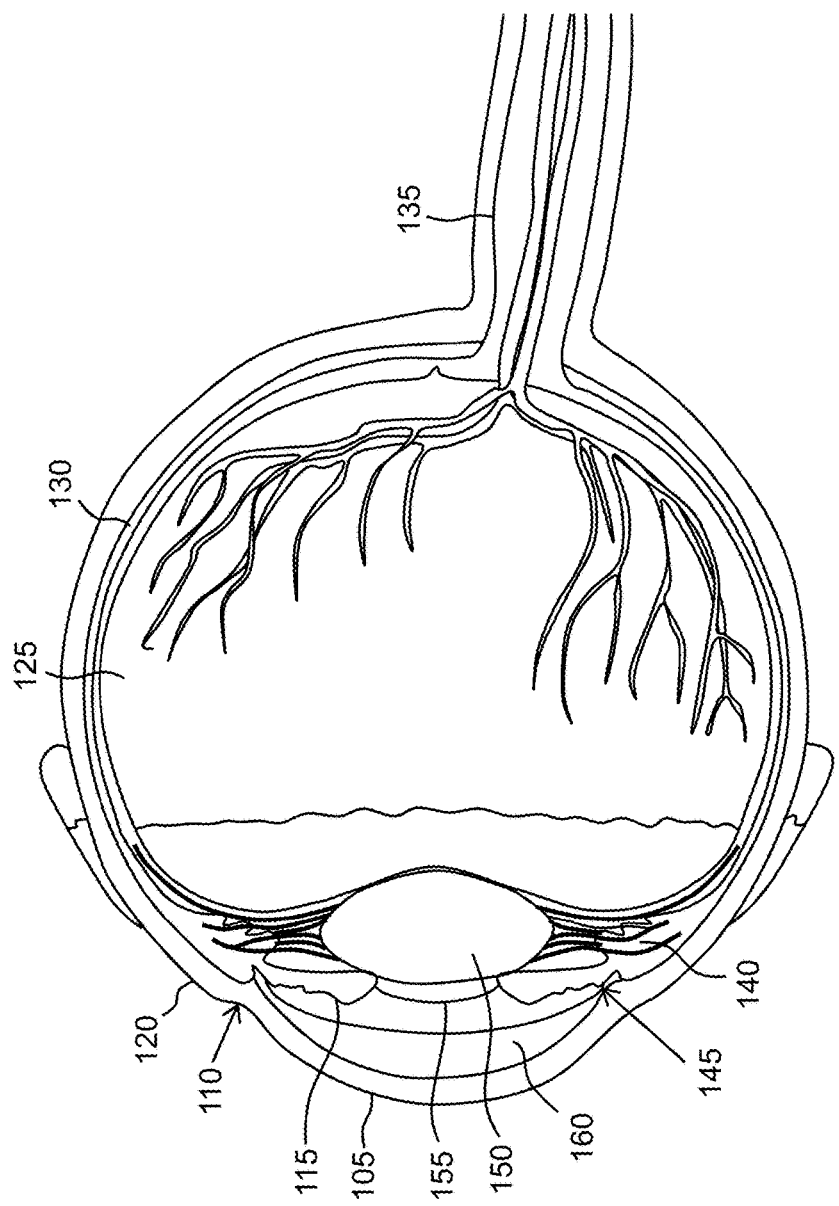
FIG. 1 is a cross-sectional view of a mammalian eye.

To overcome the difficulties outlined above, the present application discloses a microshunt device and method of treatment for glaucoma that diverts aqueous humor from the anterior chamber to the surface of the cornea. The exterior surface of the cornea is a readily-accessible site for long-term extraocular diversion of aqueous fluid from within the eye for the purpose of controlling glaucoma. Additionally, the present application provides for a microshunt to be implanted into the cornea so that aqueous fluid may be drained from the anterior chamber to the surface of the cornea, via the microshunt, such that the microshunt is prevented from migrating from its implantation site, for example, with a silver anti-microbial core, and an optional temporary flow-restricting member designed to (a) control globe decompression after the microshunt is implanted; (b) control flow of aqueous out of the eye; and (c) in the event of microshunt plugging, may be used to restore microshunt patency.

Some embodiments of the apparatus for inserting a glaucoma implant in the cornea of the eye may include devices and methods for treatment of intraocular pressure due to glaucoma. A hollow microshunt may be adapted for implantation within the cornea of an eye such that aqueous humor flows controllably from an anterior chamber of the eye to the anterior surface of the cornea, bypassing the trabecular meshwork. In one embodiment, the microshunt may comprise a quantity of antimicrobial pharmaceuticals to reduce the possibility of corneal and/or intraocular infection.

A corneal implant device, and the method and apparatus for inserting the microshunt implant into the cornea of the eye is disclosed herein. The corneal implant may include a small hole, cavity, orifice, or group of orifices that allow leakage of fluid from the eye onto the surface of the cornea. The rate of leakage of fluid from the eye may be intended, by design of the implant, to match the normal production of fluid by the eye such that pressure buildup associated with glaucoma is controlled to an acceptable pressure level. One embodiment of the corneal implant may comprise a wire or partial plug element that is coaxially located within the implant device. The wire or plug element may be one of many possible materials including silver metal. Another embodiment of the corneal implant may allow the adjustment of leakage rate by removing the coaxial element and substitution of either a smaller or larger element; where the diameter of the element may affect the size of the orifice and thereby the fluid flow. The implant may also be designed to allow fluids of all types to be injected through the corneal implant into the interior of the eye. Accordingly, the implant may facilitate the flow of fluid on both directions, i.e., in and out of the eye.

One embodiment of the apparatus for inserting a glaucoma implant in the cornea of the eye provides a microshunt that is implantable within a cornea. The microshunt may comprise an inlet section comprising at least one lumen and one inlet opening, an outlet section having at least one lumen that connects to at least one outlet opening, where the lumen is an inside space of a tubular structure. In one embodiment, the microshunt may further comprise a flow-restricting member within the lumen that is configured to permit fluid entering the lumen of the inlet section to pass through the flow-restricting member, enter the lumen of the middle section, pass into the lumen of the outlet section, and then exit the outlet section.

Other embodiments of the apparatus for inserting a glaucoma implant in the cornea of the eye, may provide an apparatus for implanting a microshunt within a cornea such that the implant is placed through the cornea to drain aqueous from the anterior chamber to the surface of the cornea. The apparatus may comprise a syringe portion and a cannula portion that has proximal and distal ends. The proximal end of the cannula portion is attached to the syringe portion. The cannula portion further comprises a first lumen and at least one irrigating hole disposed between the proximal and distal ends of the cannula portion. The irrigating hole is in fluid communication with the lumen. The apparatus further includes a holder including a second lumen for holding the microshunt. A distal end of the second lumen opens to the distal end of the cannula portion, and a proximal end of the second lumen may be separated from the first lumen of the cannula portion. The holder may function to hold the microshunt during implantation of the device within the eye, and the holder releases the microshunt when a practitioner activates deployment of the device. In some embodiments fluid is infused through a lumen of the microshunt into the anterior chamber In one embodiment, the apparatus for inserting a glaucoma implant in the cornea of the eye may be arranged where the fluid is at least one of a salt solution or viscoelastic. Optionally, the fluid may comprise a therapeutic substance such as a pharmaceutical, a gene, a growth factor, and/or an enzyme. In other embodiments, the fluid may comprise a therapeutic substance such as an antiglaucoma drug, a beta-adrenergic antagonist, a TGF-beta compound, and/or an antibiotic. In yet other embodiments, the infusing lumen of the microshunt device may further comprise coupling the inflow portion of the microshunt with a fluid delivery element that transmits the fluid to the microshunt. Optionally, the apparatus for inserting a glaucoma implant in the cornea of the eye may be so that the coupling comprises securing a screw thread arrangement of the fluid delivery element with a receiving thread arrangement of the microshunt.

The present application may generally relate to medical devices and method for continuously decompressing elevated intraocular pressure in eyes affected by glaucoma and/or for treatment of dry eye by diverting aqueous humor from the anterior chamber of the animal eye onto the surface of the cornea through a surgically implanted shunt. The shunt devices may provide uni-directional or bi-directional flow of fluid through the cornea. The shunt may include a silver-lined hollow tube and/or a silver-impregnated antimicrobial material, having a length sufficient to span the distance between the corneal endothelial surface and the outside of the cornea, and a seal device to anchor the shunt device within the cornea. In some embodiments, the shunt may also include a fluid pressure openable valve or a sphincter valve in the tube, allowing for controlled flow of aqueous humor from the anterior chamber through the tube on to the corneal surface when implanted.

In one embodiment, the apparatus may include a handpiece device to implant the microshunt; where the handpiece may have a distal end and a proximal end; a (sharp) tip connected to the distal end of the handpiece, the sharp tip having a distal portion and being configured to perform a corneal incision and into the anterior chamber of the eye; a holder attached to the distal portion of the elongate tip, the holder configured to hold and release the microshunt; and an actuator on the handpiece that actuates the holder to release the microshunt from the holder into the cornea.

Embodiments of the present application further describe surgical and therapeutic treatment of glaucoma through reduction of intraocular pressure via the use of the microshunt. While the description sets forth various embodiment specific details, the description is illustrative only and should not be construed in any way as limiting the invention. Furthermore, various applications of the invention, and modifications thereto, which may occur to those who are skilled in the art, are also encompassed by the general concepts described below.

Figure 2:
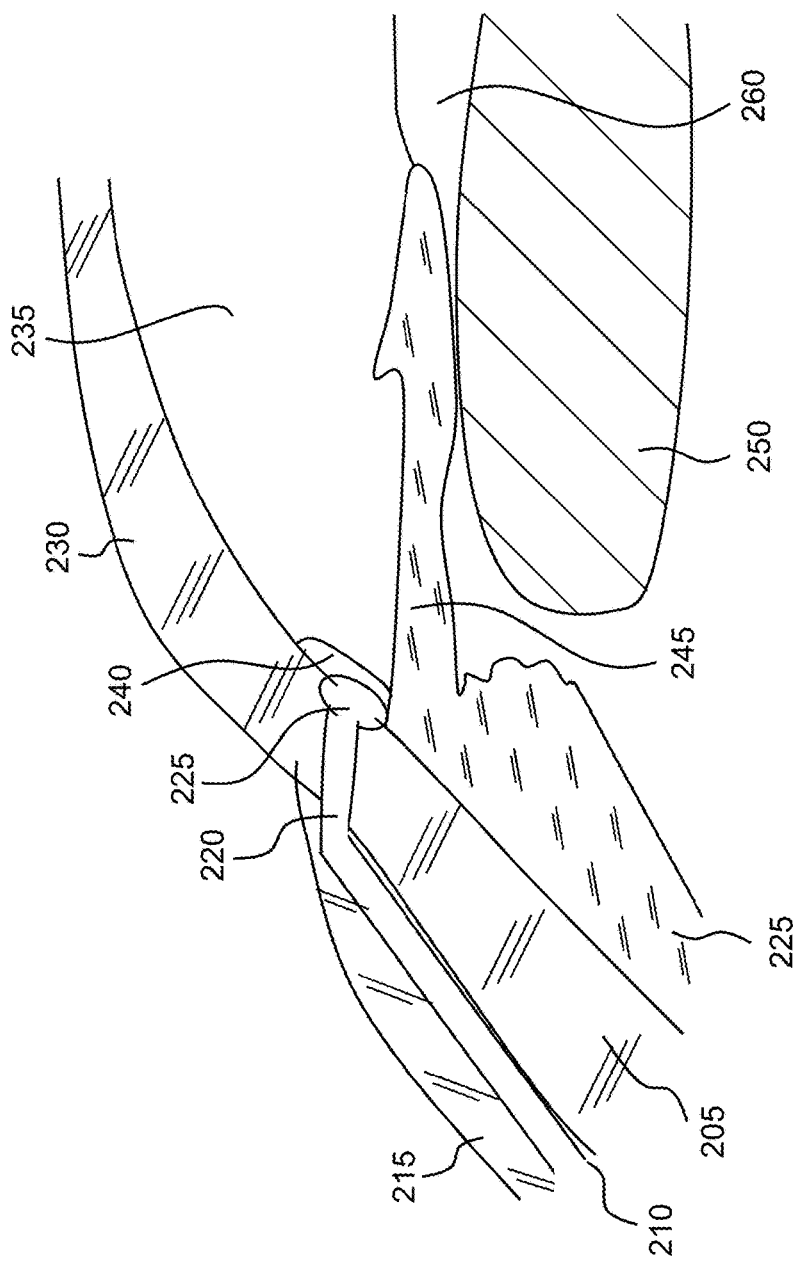
FIG. 2 is a close-up view showing the relative anatomical locations of the trabecular meshwork, the anterior chamber, and the cornea.

FIG. 1 is a cross-sectional view of a mammalian eye, while FIG. 2 is a close-up view showing the relative anatomical locations of the trabecular meshwork (145), the anterior chamber (160), and the cornea (105). The sclera (120) is a thick collagenous tissue that covers the entire eye except a portion that is covered by the cornea (105). The cornea (105) is a thin transparent tissue that focuses and transmits light into the eye and through the pupil (155), which is a circular hole in the center of the iris (115) (colored portion of the eye). The cornea (105) merges into the sclera (120) at a juncture referred to as the limbus (110). The ciliary body (140) extends along the interior of the sclera and is coextensive with the choroid (130). The choroid (130) is a vascular layer of the eye, located between the sclera (120) and the retina (125). The optic nerve (135) transmits visual information to the brain and is the anatomic structure that is progressively damaged by glaucoma.

Figure 3:
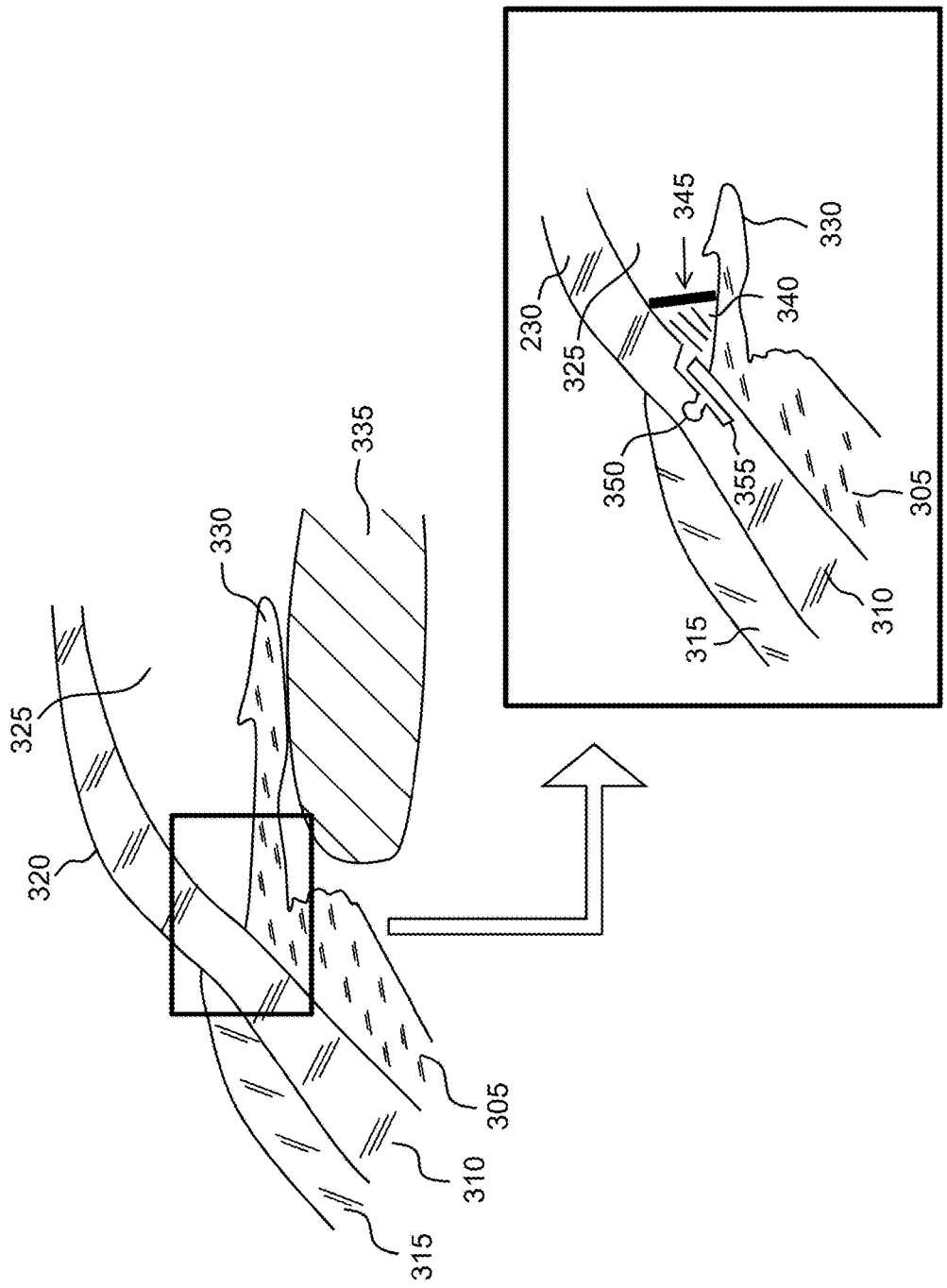
FIG. 3 is a cross-sectional view of the non-primate mammalian drainage angle.

FIG. 2 is a cross-sectional view of a primate drainage angle; as shown in FIGS. 2 and 3, the anatomy of the drainage angle of the primate eye (FIG. 2) is considerably different from the anatomy of the drainage angle of the non-primate mammalian eye (FIG. 3). The anterior chamber (235) of the eye, which is bound anteriorly by the cornea (230) and posteriorly by the iris (245) and the lens (250), is filled with aqueous humor (hereinafter referred to as "aqueous"). Aqueous is produced by the ciliary body (255), then moves anteriorly through the pupil (260) and reaches the anterior chamber angle, formed between the iris and the cornea. In a normal eye, aqueous is removed from the anterior chamber through the trabecular meshwork (240). Aqueous passes through the trabecular meshwork into Schlemm's canal (225) and thereafter through a plurality of aqueous collector veins (220), which merge with episcleral blood-carrying veins (210), and into systemic venous circulation. Intraocular pressure is maintained by an intricate balance between secretion and outflow of aqueous in the manner described above. Glaucoma is, in most cases and as described previously, characterized by an excessive buildup of aqueous in the anterior chamber, which leads to an increase in intraocular pressure. Fluids are relatively incompressible, and thus intraocular pressure is distributed uniformly throughout the eye.

Traditional procedures that create a hole or opening for implanting a device through the tissues of the conjunctiva (215) and sclera (205), or inserting a microshunt through trabecular meshwork (240) having a distal portion disposed within Schlemm's canal (225) and a proximal portion disposed within the anterior chamber of the eye (235), involve extensive surgery, as compared to surgery for implanting a device, as described herein, which ultimately resides entirely within the confines of the cornea (230).

FIG. 3 is a cross-sectional view of the non-primate mammalian drainage angle. The anterior chamber (325) of the eye, which is bound anteriorly by the cornea (320) and posteriorly by the iris (330) and the lens (335), is filled with aqueous humor (hereinafter referred to as "aqueous"). Aqueous is produced by the ciliary body (305), then moves anteriorly through the pupil (360) and reaches the anterior chamber angle, formed between the iris and the cornea. Aqueous drains between pillars of tissue (pectinate ligaments) (345) as the most anterior part of the iridocorneal angle, which communicate with a wide region (the ciliary cleft) (340) that drains aqueous into the uveal and corneoscleral trabecular meshwork. From there, aqueous enters into one or more drainage veins that comprise the angular aqueous plexus (AAP) (355), and then exits the eye via the intrascleral venous plexus (350) which drain into episcleral veins between the sclera (310) and the conjunctiva (315). Note the absence of a Schlemm's canal in the non-primate mammalian drainage angle.

Figure 4B:
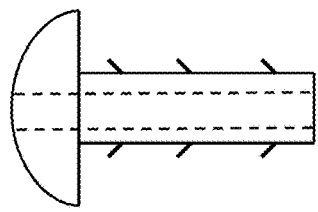
FIGS. 4A-F show a detailed external view of various embodiments of a microshunt.
Figure 4C:
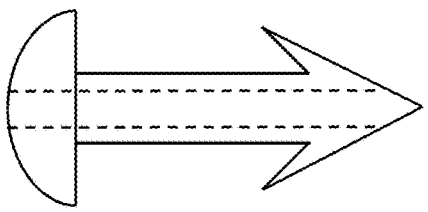
Figure 4E:
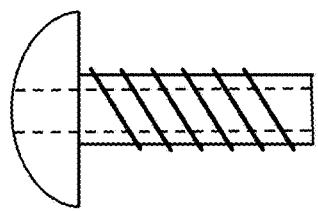
Figure 4F:
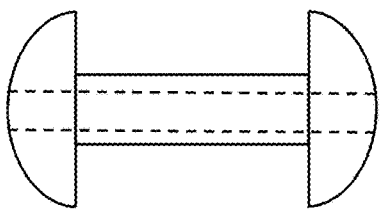
Figure 4A:
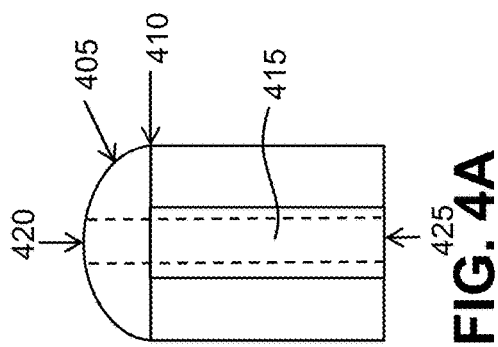
Figure 4D:
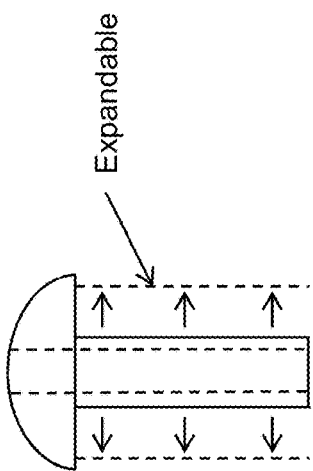

FIG. 4A depicts an embodiment of a hollow microshunt (405) that may be used in order to facilitate/effect the outflow of aqueous from the anterior chamber through the cornea onto the surface of the cornea (410), and so that the intraocular pressure is reduced. In a cross-section of the illustrated embodiment, the microshunt comprises an inlet section, having an inlet opening (425), a middle section (415), and an outlet section (420) having at least one opening. The middle section (415) may be an extension of, or may be coextensive with, the inlet section. The device comprises at least one lumen within section, which is in fluid communication with the inlet opening and the outlet opening thereby facilitating transfer of aqueous through the device.

The lumen and the remaining body of the outlet section may have a cross-sectional shape that is oval, circular, or other appropriate shape. In one embodiment, the middle section may have a length that is roughly slightly larger than the thickness of the cornea, which typically ranges between about 400 µm and about 800 µm.

To further stent, shunt, or open the outflow pathway after implanting the microshunt, a plurality of elevated, that is, protruding axially, supports or pillars may be located at the distal-most end of the outlet section sized and configured for allowing media, for example, aqueous, liquid, balanced salt solution, viscoelastic fluid, therapeutic agents, or the like, to be transported freely.

The microshunt may further comprise a flow-restricting member (see FIG. 6C, ref no. 655), which is tightly retained within a lumen. The flow-restricting member is sized and configured for maintaining a safe (normal) intraocular pressure of the fluid within the anterior chamber for a suitable period of time. Alternatively, the flow-restricting member may be situated in any location within the device such that fluid flow is restricted such that intraocular pressure is maintained at a safe level within the anterior chamber. The flow-restricting member may, in other embodiments, be a filter made of a material selected from, but not limited to, the following filter materials: expanded polytetrafluoroethylene, cellulose, ceramic, glass, Nylon, plastic, and fluorinated material such as polyvinylidene fluoride ("PVDF").

The microshunt allows leakage from the higher pressure environment, i.e., eye interior, to the lower pressure environment, i.e., eye exterior. The microshunt device may incorporate a small orifice or series of orifices arranged either in series or parallel or a combination thereof. The calculated effective orifice size may have a 0.001 inch diameter. An exemplary method to control the fluid flow may be one in which a small effective diameter hole may be created by partially filling an initial hole or orifice (see FIG. 6C, ref no. 665) with a plug element. The plug element may, for example, comprise a fine diameter wire where the diameter of the wire is less than the diameter of the initial hole or orifice. A plug may also allow the microshunt performance to be fine-tuned prior to surgical implantation or allow a microshunt assembly to be tuned after surgery. In one embodiment, the effective orifice may even be a fused filter material. Optionally, a tool may be designed that may hold the microshunt body and allow a plug element to be removed and replaced with a different plug element having a different diameter, for example, that might be smaller or larger than the original plug.

The microshunt may be made by, for example, molding, thermo-forming, sintering, or other micro-machining techniques. The microshunt may comprise a biocompatible material such that inflammation arising due to irritation between the outer surface of the device and the surrounding tissue is minimized. Biocompatible materials which may be used for the device may include, but are not limited to, titanium, stainless steel, medical grade silicone, e.g., Silastic™, available from Dow Corning Corporation of Midland, Mich.; and polyurethane, e.g., Pellethane™, also available from Dow Corning Corporation. In other embodiments, the device may comprise other types of biocompatible material, such as, by way of example, polyvinyl alcohol, polyvinyl pyrolidone, collagen, heparinized collagen, polytetrafluoroethylene, expanded polytetrafluoroethylene, fluorinated polymer, fluorinated elastomer, flexible fused silica, polyolefin, polyester, polysilicon, and/or a mixture of the aforementioned biocompatible materials, and the like. In another embodiment, the microshunt may be made of a biodegradable material selected from a group consisting of poly (lactic acid), polyethylene-vinyl acetate, poly (lactic-co-glycolic acid), poly (D,L-lactide), poly (D,L-lactide-co-trimethylene carbonate), poly (caprolactone), poly (glycolic acid), and copolymer thereof. In other embodiments, composite biocompatible material may be used, wherein a surface material may be used in addition to one or more of the aforementioned materials. For example, such a surface material may include polytetrafluoroethylene (PTFE) (such as Teflon™), polyimide, hydrogel, heparin, therapeutic drugs (such as beta-adrenergic antagonists, TGF-beta, and other anti-glaucoma drugs, or antibiotics), and similar material.

As is well known in the art, a device coated or loaded with a slow-release substance may have prolonged effects on local tissue surrounding the device. The slow-release delivery may be designed such that an effective amount of substance is released over a desired duration. "Substance," as used herein, is defined as any therapeutic or active drug that may stop, mitigate, slow-down or reverse undesired disease processes.

In one embodiment, the device may be made of a biodegradable—also including bio-erodible—material admixed with a substance for substance slow-release into ocular tissues. In another embodiment, polymer films may function as substance containing release devices whereby the polymer films may be coupled or secured to the device. The polymer films may be designed to permit the controlled release of the substance at a chosen rate and for a selected duration, which may also be episodic or periodic. Such polymer films may be synthesized such that the substance is bound to the surface or resides within a pore in the film so that the substance is relatively protected from enzymatic attack. The polymer films may also be modified to alter their hydrophilicity, hydrophobicity and vulnerability to platelet adhesion and enzymatic attack. The device may be used for a direct release of pharmaceutical preparations into ocular tissues. As discussed above, the pharmaceuticals may be compounded within the device or form a coating on the device. Any known drug therapy for glaucoma may be utilized.

FIGS. 4B-F depict a detailed external view of the microshunt. In some aspect, the proximal section may have a bottom peripheral surface that is perpendicular to the lumen of the microshunt. A receiving thread arrangement may be appropriately located on the peripheral surface. The receiving thread arrangement may be sized and configured to releasably receive a screw thread arrangement for coupling together, wherein the screw thread arrangement may be disposed at the distal end of a fluid delivery element which has a lumen for transporting the infusing fluid into the aqueous cavity for therapeutic purposes. In one embodiment, the coupling of the receiving thread arrangement and the screw thread arrangement effects the fluid infusion through the lumen leak-proof.

In one embodiment, the outlet side openings, each of which may be in fluid communication with the lumen for transmission of aqueous, may be arranged spaced apart around the circumferential periphery of the outlet section.

Figure 5:
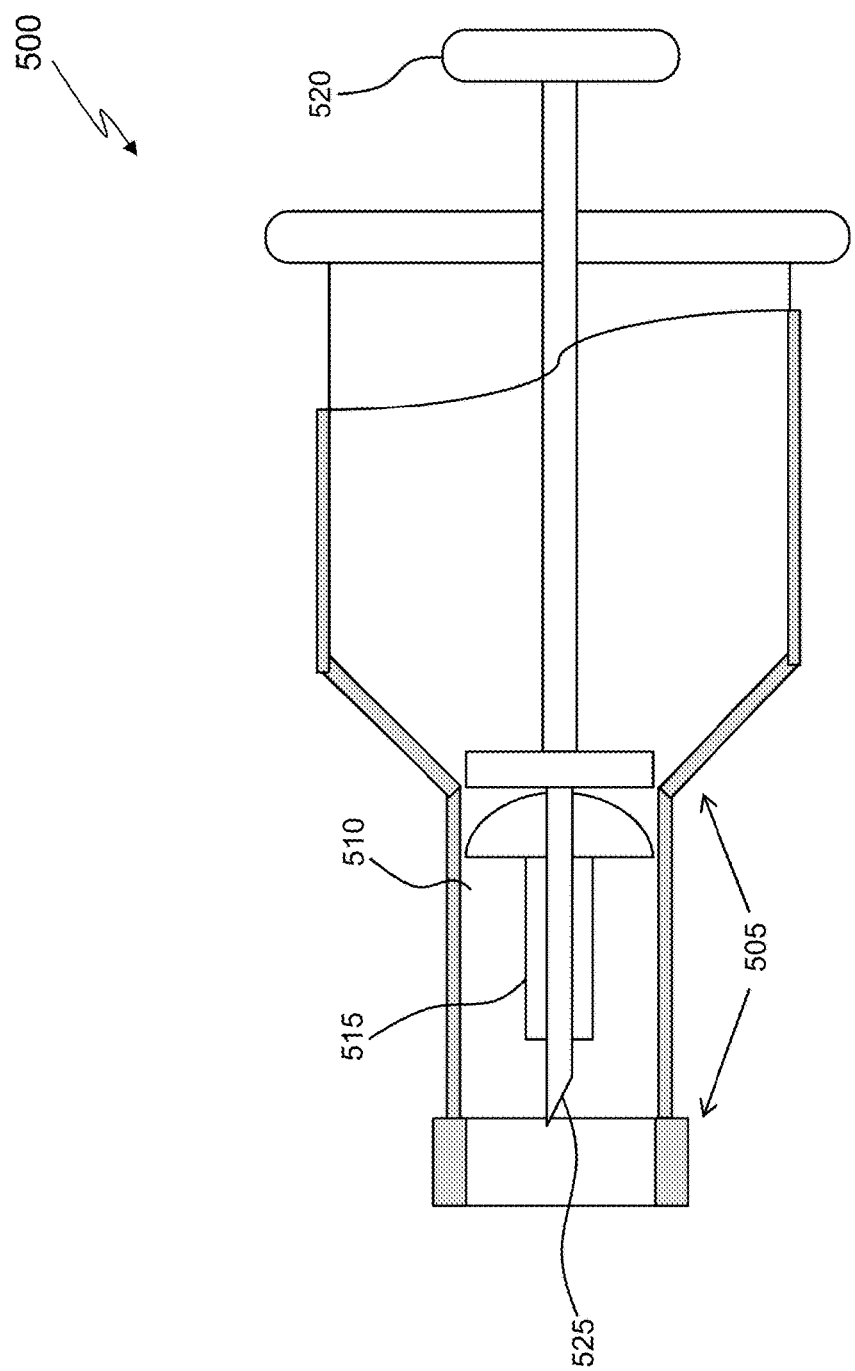
FIG. 5 shows an embodiment of an applicator for delivering a microshunt into the cornea.

FIG. 5 shows an embodiment of an applicator (500) for delivering a microshunt into the cornea, the applicator having a fixture body (505). The distal portion comprises a cutting means (525) sharp enough for creating an incision in and through the cornea for the microshunt (515) placement. The microshunt may be tightly placed within the cannula lumen (510) of the applicator and retained by a plunger-type (520) deployment mechanism. The microshunt is deployed from the applicator once the distal section passes beyond the corneal endothelium and into the anterior chamber. In one aspect, the microshunt deployment may be facilitated by the plunger-type deployment mechanism with an associated deployment actuator mounted on the handle of the applicator. The microshunt may be releasably coupled with a fluid restricting or fluid delivery element at any convenient time during the procedure. In one aspect, the screw-unscrew coupling steps between the microshunt and the fluid delivery element may be carried out by suitably rotating the fluid restricting or fluid delivery element with reference to the microshunt receiving thread arrangement.

In one embodiment, the microshunt device may have a length ranging from about 300 um to over 1000 um. Optionally, the device may have an outside diameter ranging between about 30 µm and about 500 µm, with the lumen having an exemplary set of diameters ranging between about 20 µm and about 250 µm, respectively. In addition, the device may have a plurality of lumens to facilitate transmission of multiple flows of aqueous or infusing fluid.

In a method embodiment for increasing aqueous outflow in the eye of a patient, to reduce intraocular pressure therein, the method may comprise the step of bypassing the trabecular meshwork. While in use, the device may be placed through the cornea, through a slit or opening. This opening may be created by use of a laser, a knife, thermal energy (radiofrequency, ultrasound, and microwave), cryogenic energy, or any other available surgical cutting instrument. The opening may also be horizontal or substantially horizontal, i.e., extending longitudinally in the same direction as the circumference of the limbus (see FIG. 1). Other opening directions may also be used, depending on the set of circumstances. The opening may be oriented at any angle, relative to the circumference of the limbus that is appropriate for inserting the device through the cornea and into the anterior chamber.

Figure 6C:
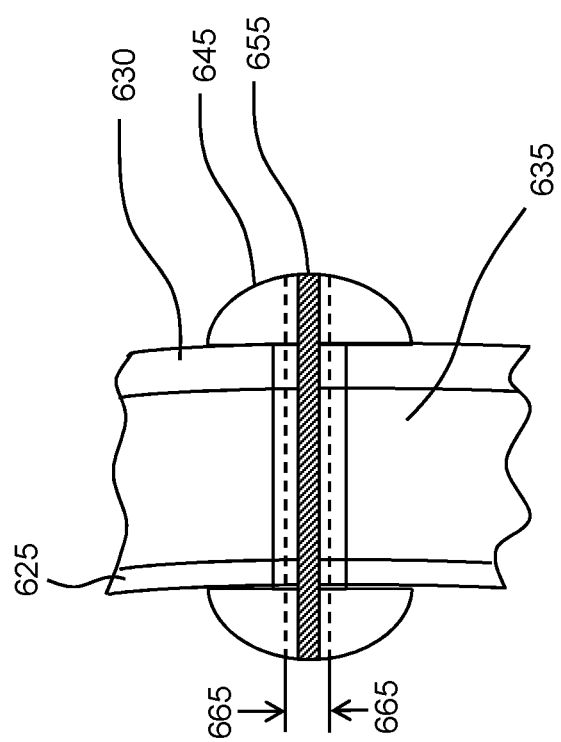
FIG. 6C depicts a side view of a method by which the microshunt is implanted within the cornea.

FIGS. 6A-C generally illustrate a method by which the microshunt (645) may be implanted within the cornea. FIG. 6A depicts a front view and FIGS. 6B and 6C depict a side view. In the illustrated method, a delivery applicator is provided, which preferably comprises a syringe portion and a cannula portion, which may comprise at least one lumen in fluid communication with the aqueous fluid coming from the eye. A holder at the distal portion of the cannula portion for holding the device may comprise a lumen, a sheath, a clamp, tongs, a space, and any other available means for holding the device. In the method illustrated in FIG. 6B, the device may be placed into the lumen of the delivery applicator (640) and then advanced to a desired implantation site within the cornea (605). The delivery applicator may then hold the device securely during delivery and may release it when the practitioner initiates deployment actuator of the applicator. The device may be placed against the epithelial surface of the cornea (630), and inserted through the corneal stroma (635) and endothelium (625) so that the lumen of the microshunt communicates with the aqueous in the anterior chamber (620).

The microshunt device may be retained by the corneal tissue. The microshunt device body may have a geometry that may restrict the microshunt device from moving either into or out of the eye after surgical implantation. Alternately, the microshunt device body may have a roughness, radial ridges, helical ridge or similar feature that causes the microshunt device body to remain fixed under the very slight hydrostatic pressure associated with the glaucomatous condition. The microshunt device may be designed to undergo a geometry change during implanting in order to achieve the retention due to geometry features. The cornea may be surgically cut during implantation and allow the microshunt device geometry to be of a fixed type with the cornea healing to form the desired retention.

In one embodiment of the microshunt corneal surgery, a patient may be placed in an appropriate position, prepped, draped, and appropriately anesthetized. A small incision may then be made through the cornea with a self-trephining applicator. The incision may for example have a surface length less than about 1.0 millimeter in length. Through the corneal incision, the anterior chamber may be accessed, thereby forming a through the cornea for stent placement. After the device is appropriately implanted, the applicator may be withdrawn and the corneal microshunt surgery may be concluded.

In some aspect of the microshunt corneal surgery, a method may be presented where fluid may be injected through the microshunt into the anterior chamber. In one embodiment of the microshunt device a method for using a removable applicator, catheter, cannula, or tubing that is placed ab interno through the microshunt into the anterior chamber of an eye adapted for infusing therapeutic liquid into the aqueous cavity may be used. The fluid may be a salt solution such as Balanced Salt Solution, a viscoelastic, any other suitable viscous or non-viscous liquid, or suitable liquid loaded with drug at a concentration suitable for therapeutic purposes without causing safety concerns. A combination of liquids may also be used. The pressure is raised at an appropriate rate of rise to an appropriate level and for an appropriate length of time, as determined through development studies, to provide for the expansion of the outflow structures and/or a clearing of any blockages within them. The procedure may be augmented with other aids to enhance its effectiveness. These aids may include heat, vibration (sonic or ultrasonic), pulsation of a pressure front, pH, drugs, etc.

The disclosed embodiments of the microshunt device may provide a method to simplify microshunt corneal surgeries. Accordingly, the surgery may potentially be performed on an outpatient basis under topical or local anesthesia, or with a brief general anesthesia, with improved prognosis for retaining vision, greatly reduced morbidity and expense. The method and device may be used for short-term or long-term control of glaucoma in all species of animals, especially, dogs, cats, and horses, including humans.

It is contemplated that various combinations and/or subcombinations of the specific features and aspects of the above embodiments may be made and still fall within the scope of the invention. Accordingly, it should be understood that various features and aspects of the disclosed embodiments may be combined with or substituted for one another in order to form varying modes of the disclosed invention. Further it is intended that the scope of the present invention herein disclosed by way of examples should not be limited by the particular disclosed embodiments described above

What is claimed is:

1. A system comprising:
    a barrel holder, wherein the holder has a proximal end and a distal end, wherein the proximal end of the holder contains a plunger and the distal end contains an extrusion tip;
        wherein the extrusion tip further comprises a first lumen and at least one hole disposed between the proximal and distal ends of the extrusion tip;
        wherein fluid is infused through a lumen of the microshunt device into the anterior chamber;
    a microshunt device, wherein the microshunt device is configured to be implanted within a cornea of an eye, and wherein the microshunt device effects the flow of aqueous humor from an anterior chamber of the eye to the anterior surface of the cornea, bypassing the trabecular meshwork; and
    a barrel holder comprising a second lumen, wherein a distal end of the second lumen opens to the distal end of the extrusion tip portion; and wherein the holder is configured to hold the microshunt device during implantation of the microshunt device within the eye, and the holder releases the microshunt device upon deployment of the microshunt device.

2. The system of claim 1 wherein the proximal end of the second lumen is separated from the first lumen of the extrusion tip.

3. The system of claim 1 further comprising a flow-restricting member configured to:
    control globe decompression after the microshunt device is implanted; and
    control flow of aqueous out of the eye.

* * * * *